US00PP19242P2

(12) United States Plant Patent
Mehring-Lemper

(10) Patent No.: US PP19,242 P2
(45) Date of Patent: Sep. 16, 2008

(54) *LEUCANTHEMUM* PLANT NAMED 'LEUMAYEL'

(50) Latin Name: *Leucanthemum maximum*
Varietal Denomination: Leumayel

(75) Inventor: Manfred Mehring-Lemper, Hann. Münden (DE)

(73) Assignee: Syngenta Seeds B.V., Enkhuizen (NL)

( * ) Notice: Subject to any disclaimer, the term of this patent is extended or adjusted under 35 U.S.C. 154(b) by 164 days.

(21) Appl. No.: 11/500,221

(22) Filed: Aug. 7, 2006

(51) Int. Cl.
*A01H 5/00* (2006.01)

(52) U.S. Cl. ..... Plt./263.1
(58) Field of Classification Search ..... Plt./263.1
See application file for complete search history.

(56) References Cited

PUBLICATIONS

GTITM UPOVROM Citation for 'Leumayel' as per CA PBR 05–4771; Apr. 22, 2005.*

* cited by examiner

*Primary Examiner*—Kent L Bell
(74) *Attorney, Agent, or Firm*—S. Matthew Edwards

(57) ABSTRACT

A new *Leucanthemum* plant characterized particularly as to novelty by its big, single flowers with light-yellow flower color.

1 Drawing Sheet

Latin name of the genus and species of the plant claimed: *Leucanthemum maximum.*
Varietal denomination: 'Leumayel'.

BACKGROUND OF THE NEW PLANT

The present invention comprises a new distinct cultivar of *Leucanthemum,* botanically known as *Leucanthemum maximum.*

The new *Leucanthemum* is a product of a planned breeding program conducted in Hannover-Münden, Germany. The new *Leucanthemum* cultivar is floriferous, single-flowering, with yellowish flower color, good flower quality and a good vigor.

The present cultivar originated from a cross made in 1999 of a *Leucanthemum* selection identified as 'S055,' not patented, as the female, or seed parent, with a *Leucanthemum* population identified as '65-86,' not patented, as the male, or pollen parent.

The present cultivar has been repeatedly asexually reproduced by cuttings in Hannover-Münden, Germany, in Enkhuizen, Netherlands, in Angers, France, and in Gilroy, USA since September 2000.

The distinctive characteristics of this new *Leucanthemum* are stable and reproduced true to type in successive generations of asexual reproduction. It takes 16 to 18 weeks to produce a finished plant, depending on the temperature.

This new *Leucanthemum* plant is a perennial in all climatical zones in the US.

DESCRIPTION OF THE DRAWING

This new *Leucanthemum* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Leucanthemum.* The data which defines these characteristics were collected from asexual reproductions carried out in Enkhuizen, Netherlands. The plant description was taken on 26 week old plants, blossomed under natural light in the greenhouse.

No detailed information is available on the difference between plants of the new *Leucanthemum* and the plants of the female parent selection, since the female parent selection is a heterogeneous genetic pool.

No detailed information is available on the difference between plants of the new *Leucanthemum* and the plants of the male parent selection, since the male parent selection is a heterogeneous genetic pool.

Natural flowering season at specified location(s):

Under Northern European conditions, 'Leumayel' flowers from June until the end of the Summer.

The following traits distinguish 'Leumayel' as a new and distinct cultivar:

The ray floret color is light-yellow.

The inflorescences are single.

The inflorescences have a very big size.

TABLE 1

DIFFERENCES BETWEEN THE NEW CULTIVAR 'LEUMAYEL' AND A SIMILAR CULTIVAR

| | 'Leumayel' | 'Leukal' (U.S. Plant Patent No. 15,204) |
|---|---|---|
| Inflorescence type | Single flowering | Double flowering |
| Ray floret color when opening | Less yellow (3D) | More yellow (7D) |

THE PLANT

Parentage:
*Female parent.*—'S055,' a genetic pool-selection, not patented.
*Male parent.*—'65-86,' a genetic pool-selection, not patented.
Propagation:
*Type cutting.*—Terminal cuttings.
*Time to initiate roots.*—21 days at 20° C.
*Time to produce a rooted cutting.*—6 weeks.
*Root description.*—Fine, fibrous and white in color.
Plant description:
*General appearance.*—Heavy, sturdy plant with dark leaves and big inflorescences.
*Branching habit.*—Basal branching.
*Plant height.*—45 cm.
*Plant spread.*—30 cm.
Lateral branch description:
*Length.*—Primary: 36 cm, Secondary: 12 cm.
*Diameter.*—Primary: 0.5 cm, Secondary: 0.3 cm.
*Texture.*—Smooth, glabrous.
*Internode length.*—2 cm.
*Color.*—137C.
*Number of lateral branches per plant.*—9.
Foliage description:
*Arrangement.*—Alternate.
*Length, mature leaves.*—15 cm.
*Width, mature leaves.*—3 cm.
*Shape.*—Lanceolate.
*Apex.*—Rounded to broadly acute.
*Base.*—Attenuate.
*Aspect.*—Arcuate.
*Margin.*—Dentate.
*Pubescence.*—Upper surface: Lightly pubescent. Lower surface: Lightly pubescent.
*Texture.*—Smooth, glabrous.
*Color, young foliage, upper surface.*—RHS 137B.
*Color, young foliage, lower surface.*—137C.
*Fully expanded foliage, upper surface.*—137A.
*Fully expanded foliage, lower surface.*—138A.
*Petiole.*—Absent.
*Veins, venation type.*—Pinnate.
*Veins, color upper surface.*—143A.
*Veins, color lower surface.*—143C.
Inflorescence: Bud (described before color developed).
*Bud shape.*—Spherical.
*Bud diameter.*—1.5 cm.
*Bud length.*—0.7 cm.
*Bud color.*—137C.
Appearance:
*Form.*—Actinomorphic.
*Inflorescence position.*—Terminal.
*Disc and ray floret arrangement.*—Acropetally on a capitulum.
*Number of inflorescences per plant.*—20.
*Lasting quality.*—40 days.
*Fragrance.*—None.
Size:
*Diameter.*—11 cm.
*Height.*—2 cm
*Diameter of disc.*—3 cm. .

Ray florets:
*Length.*—4 cm.
*Width.*—0.9 cm.
*Shape.*—Oblanceolate.
*Apex.*—Tridentate.
*Base.*—Cuneate.
*Margin.*—Entire.
*Texture (both upper and lower surfaces).*—Smooth, glabrous.
*Number per inflorescence.*—48.
*Color, when opening.*—Upper surface: 3D; lower surface: 3D.
*Color, fully opened.*—Upper surface: 157D, lower surface: 155C.
Disc florets:
*Length.*—0.9 cm.
*Width.*—0.15 cm.
*Shape.*—Elliptic.
*Number per inflorescence.*—450.
*Color.*—Immature: Apex: 7A, Margin: 154C. Mature: Apex: 13B, Margin: 7B.
Phyllaries:
*Length.*—1.2 cm.
*Width.*—0.4 cm.
*Shape.*—Elliptic.
*Apex.*—Obtuse.
*Margin.*—Entire.
*Number per inflorescence.*—50.
*Arrangement.*—Imbricate whorls.
*Texture (both upper and lower surfaces).*—Smooth and glabrous with light pubescence present.
*Color.*—Upper surface: 138B, lower surface: 138B.
Peduncle:
*Length.*—8 cm.
*Diameter.*—0.4 cm.
*Aspect.*—Upright.
*Texture.*—Light pubescence present.
*Color.*—137B.
Reproductive organs:
*Androecium.*—Presence: On disc florets only. Number (per inflorescence): 1. Filament length: 0.2 cm. Filament color: 5A. Anthers: Shape: Oblong, Length: 0.1 cm, Color: 8A. Pollen: Color: 8A, Amount (generally): Moderate.
*Gynoecium.*—Presence: On disc and ray florets. Pistils: Number: 1, Length: 0.6, Style length: 0.4 cm, Color: 154C. Stigma: Shape: bi-lobed, Color: 7B.
Seeds: None observed.
Disease resistance: No resistance or susceptibility observed.
Temperature tolerance: Cold tolerance to −20 degrees C. Heat tolerance to 35 degrees C.
Drought tolerance: Not drought tolerant.

What is claimed is:

1. A new and distinct cultivar of *Leucanthemum* plant named 'Leumayel,' as substantially illustrated and described herein.

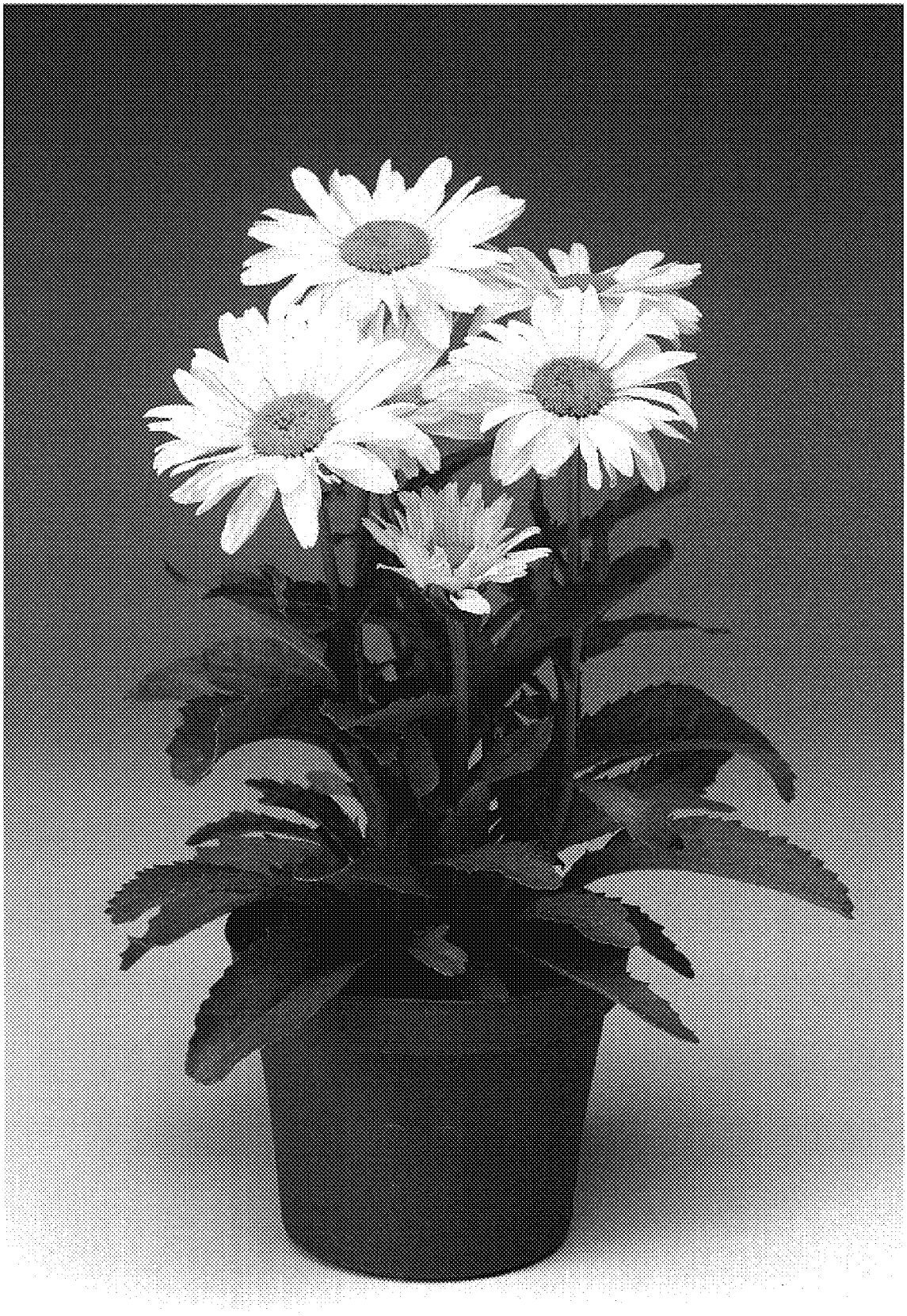

* * * * *